(12) United States Patent
Hu et al.

(10) Patent No.: US 10,223,500 B2
(45) Date of Patent: Mar. 5, 2019

(54) PREDICTING DRUG-DRUG INTERACTIONS AND SPECIFIC ADVERSE EVENTS

(71) Applicant: International Business Machines Corporation, Armonk, NY (US)

(72) Inventors: Jianying Hu, Bronx, NY (US); Yashu Liu, Tempe, AZ (US); Ping Zhang, White Plains, NY (US)

(73) Assignee: International Business Machines Corporation, Armonk, NY (US)

( * ) Notice: Subject to any disclaimer, the term of this patent is extended or adjusted under 35 U.S.C. 154(b) by 407 days.

(21) Appl. No.: 14/976,002

(22) Filed: Dec. 21, 2015

(65) Prior Publication Data

US 2017/0177803 A1    Jun. 22, 2017

(51) Int. Cl.
*G06F 19/00*    (2018.01)
*G16H 50/20*    (2018.01)

(52) U.S. Cl.
CPC ............ *G06F 19/326* (2013.01); *G06F 19/00* (2013.01); *G16H 50/20* (2018.01)

(58) Field of Classification Search
CPC .......... G06F 19/12; G06F 19/16; G06F 19/18; G06F 19/704; G06F 19/707; G06F 19/705; G06F 19/326; G16H 50/20
See application file for complete search history.

(56) References Cited

U.S. PATENT DOCUMENTS

| | | |
|---|---|---|
| 2003/0069699 A1 | 4/2003 | Ekins et al. |
| 2006/0280786 A1 | 12/2006 | Rabinow et al. |
| 2008/0126131 A1 | 5/2008 | Lou |
| 2008/0194421 A1 | 8/2008 | Borisy et al. |
| 2009/0028968 A1* | 1/2009 | Tam .................. A61K 36/48 424/757 |
| 2010/0312538 A1* | 12/2010 | Umeyama ............ C40B 30/02 703/12 |
| 2012/0232066 A1 | 9/2012 | Jenkins et al. |
| 2013/0179375 A1 | 7/2013 | Tatonetti et al. |
| 2015/0058039 A1 | 2/2015 | Shiloh |
| 2015/0106112 A1 | 4/2015 | Jackson et al. |

OTHER PUBLICATIONS

G. Jiang et al., "Mining Severe Drug-Drug Interaction Adverse Events Using Semantic Web Technologies: a Case Study," BioData Mining, Mar. 2015, 12 pages, vol. 8, No. 1.

B. Percha et al., "Informatics Confronts Drug-Drug Interactions," Trends in Pharmacological Sciences, Mar. 2013, pp. 178-184, vol. 34, No. 3.

(Continued)

*Primary Examiner* — Maroun P Kanaan

(74) *Attorney, Agent, or Firm* — Rabin Bhattacharya; Ryan, Mason & Lewis, LLP

(57) ABSTRACT

The present invention provides methods, systems and devices for drug-drug interaction and adverse event analysis. Chemical structures for one or more pairs of drugs are obtained from at least one of a user and a database. A chemical fingerprint is generated for each drug of the one or more pairs of drugs based on the chemical structure of the drug. Drug-drug interaction prediction is performed for each pair of drugs based on the chemical fingerprints. Adverse event prediction is performed based on the predicted drug-drug interaction for the one or more pairs of drugs.

17 Claims, 6 Drawing Sheets

(56) References Cited

OTHER PUBLICATIONS

S. Vilar et al., "Drug-Drug Interaction Through Molecular Structure Similarity Analysis," Journal of the American Medical Informatics Association, Nov. 2012, pp. 1066-1074, vol. 19, No. 6.
S. Vilar et al., "Detection of Drug-Drug Interactions by Modeling Interaction Profile Fingerprints," PLOS ONE, Mar. 2013, 11 pages, vol. 8, No. 3.
J. Huang et al., "Systematic Prediction of Pharmacodynamic Drug-Drug Interactions Through Protein-Protein-Interaction Network," PLOS Computational Biology, Mar. 2013, 9 pages, vol. 9, No. 3.
H. Luo et al., "DDI-CPI, a Server that Predicts Drug-Drug Interactions Through Implementing the Chemical-Protein Interactome," Nucleic Acids Research, May 2014, pp. 46-52, vol. 42.
N.P. Tatonetti et al., "Data-Driven Prediction of Drug Effects and Interactions," Science Translational Medicine, Mar. 2012, 26 pages, vol. 4, No. 125.
P. Zhang et al., "Label Propagation Prediction of Drug-Drug Interactions Based on Clinical Side Effects," Scientific Reports, Jul. 2015, 10 pages, vol. 4.
S. Vilar et al., "Similarity-Based Modeling in Large-Scale Prediction of Drug-Drug Interactions," Nature Protocols, Sep. 2014, pp. 2147-2163, vol. 8, No. 9.
A. Gottlieb et al., "INDI: a Computational Framework for Inferring Drug Interactions and Their Associated Recommendations," Molecular Systems Biology, Jul. 2012, 12 pages, vol. 8, No. 592.

* cited by examiner

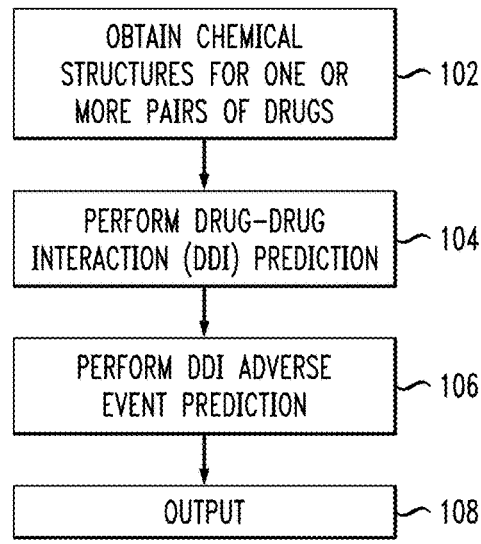
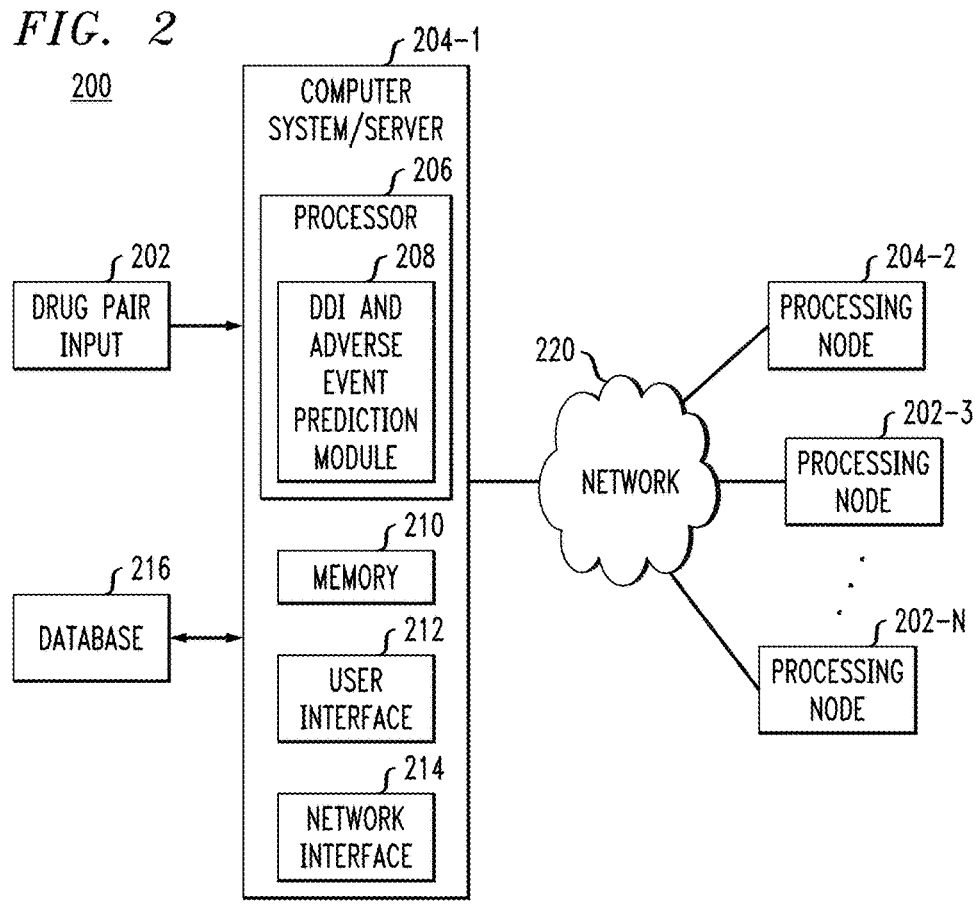

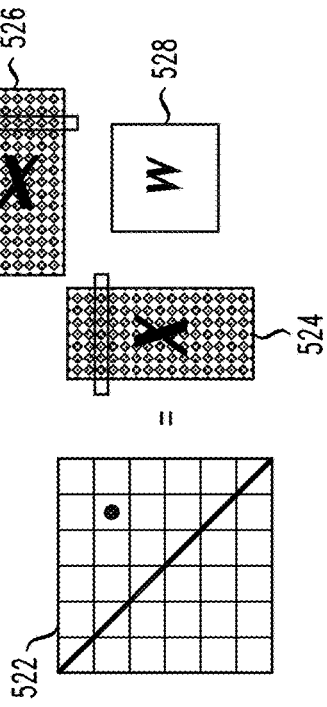
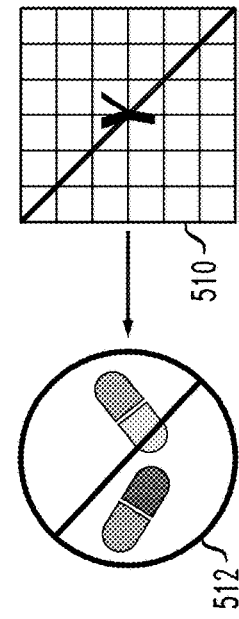
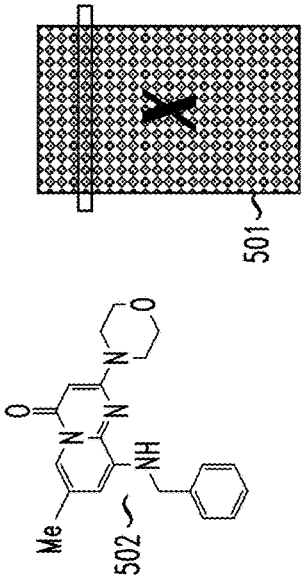
FIG. 5
Bi-LINEAR LOGISTIC REGRESSION
$$g(Y_{ij}) = x_i^T W x_j$$
DATA MATRIX:
EACH ROW, X REPRESENTS THE CHEMICAL STRUCTURE INFORMATION OF A DRUG
LABEL MATRIX:
(i, j)-th ENTRY, $Y_{ij}$, REPRESENTS THE DDI LABEL OF THE DRUG PAIR BETWEEN i-th DRUG AND j-th DRUG

PREDICTING DRUG-DRUG INTERACTIONS AND SPECIFIC ADVERSE EVENTS

BACKGROUND

The present invention relates to medication management, and more specifically, to predicting drug-drug interactions and the associated adverse events.

Commonly, patients may require treatment for a number of conditions. Consequently, the patients often require medicinal treatment involving a large number of drugs for various conditions. Drug-drug interactions (DDIs) may result when one medication interacts or intervenes with another medication. Adverse drug-drug interactions are serious health threats that can result in significant morbidity and mortality. Recent estimates indicate that DDIs cause nearly 74,000 emergency room visits and nearly 195,000 hospitalizations each year in the United States.

SUMMARY

Embodiments of the invention provide methods, systems and devices for drug-drug interaction and adverse event analysis.

According to an embodiment of the present invention a method for drug-drug interaction and adverse event analysis comprises the following steps. Chemical structures for one or more pairs of drugs are obtained from at least one of a user and a database. A chemical fingerprint is generated for each drug of the one or more pairs of drugs based on the chemical structure of the drug. Drug-drug interaction prediction is performed for each pair of drugs based on the chemical fingerprints. Adverse event prediction is performed based on the predicted drug-drug interaction for the one or more pairs of drugs.

According to another embodiment of the present invention, an apparatus for drug-drug interaction and adverse event analysis comprises a memory and a processor operatively coupled to the memory, and configured to perform one or more of the above mentioned steps.

According to yet another embodiment, a computer program product for drug-drug interaction and adverse event analysis comprises a computer readable storage medium for storing computer readable program code which, when executed, causes a computer to perform one or more of the above mentioned steps.

BRIEF DESCRIPTION OF THE DRAWINGS

FIG. 1 illustrates an overview process of a methodology for performing a DDI and adverse event analysis for one or more pairs of drugs, according to an embodiment of the invention.

FIG. 2 illustrates an exemplary embodiment of a system for implementing the methodology of FIG. 1.

FIG. 5 illustrates an exemplary bi-linear model for DDI prediction, according to an embodiment of the invention.

DETAILED DESCRIPTION

Figure 3:
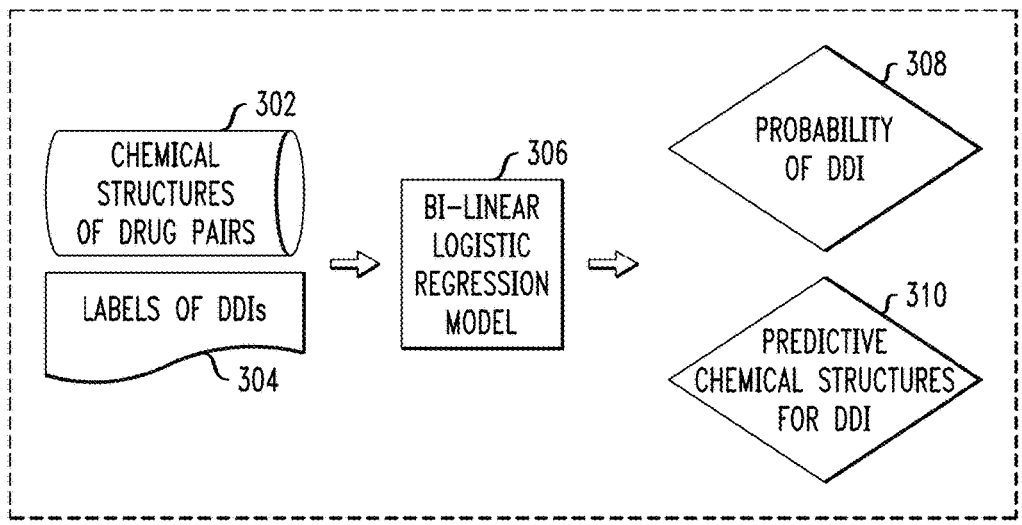
FIG. 3 illustrates an exemplary process for predicting DDI, according to an embodiment of the invention.

Illustrative embodiments of the invention may be described herein in the context of illustrative methods, systems and devices for drug-drug interaction (DDI) and adverse event analysis. However, it is to be understood that embodiments of the invention are not limited to the illustrative methods, systems and devices but instead are more broadly applicable to other suitable methods, systems and devices.

Often times, a patient may have a medication regimen that includes multiple drugs for various conditions. DDIs may result when a medication intended for treatment of one condition is in conflict with the treatment of a different condition in the same patient. For example, DDIs may occur in patients taking multiple prescription drugs and adverse events may be the result of one or more drugs interacting with, or interfering with, another drug or set of drugs, thereby resulting in, for example, decreased efficacy, toxicity, etc. In particular, elderly patients and cancer patients are typically administrated numerous medications, exposing them to a high risk of adverse events related to DDIs. Adverse drug events remain a leading cause of morbidity and mortality in the United States and around the world. As used herein, an adverse event may refer to injuries/side effects resulting from drug-related medical interventions. A DDI adverse event may be an injury resulting from occurrence of DDI between two or more drugs. Examples of DDI adverse events may include, headaches, nausea, vomiting, bleeding, death, etc.

As such, avoiding drug conflicts, such as potential DDIs, may increase the safety and efficacy of medications used by patients. While large collections of adverse drug event reports are maintained by the Food and Drug Administration (FDA) and other organizations, existing approaches to DDI discovery, which include Phase IV clinical trials and post-marketing surveillance, are insufficient for detecting many DDIs and do not alert the public to potentially dangerous DDIs before a drug enters the market.

Furthermore, existing methods are unable to: (1) predict specific adverse events of DDIs; (2) account for tasks of predicting related adverse events of DDIs (as a symptom might be associate with other symptoms in the real-world); (3) learn related tasks simultaneously by extracting and utilizing appropriate shared information across tasks; (4) systemically analyze "incompatible" chemical fingerprints for DDIs and for specific adverse events.

Embodiments herein provide for a cascade method and system for predicting drug-drug interactions and their specific adverse events. At the first level, a feature-vector based bi-linear method (e.g., using a bi-linear model) is used to predict whether a drug interacts with another drug. At the second level, a multi-task bi-linear model is used to predict specific adverse events for each possible DDI. Various embodiments herein may systematically generate insights about chemical fingerprints for DDIs and their specific adverse events.

Referring to the figures, FIG. 1 depicts an overview of a methodology 100 for obtaining a pair of drugs and performing DDI and adverse events analysis on the pair of drugs, according to an embodiment. At step 102, chemical structures for one or more pairs of drugs (i.e., two drugs of different chemical composition) are received. As used herein with respect to steps performed in conjunction with a computing system, a chemical structure may refer to a computer readable representation of the molecular geometry and/or composition of a compound (e.g., a drug). The chemical structures of the drug pair(s) may be obtained, for example, via user input at a graphical user interface (GUI). Alternatively, the user may enter one or more pairs of drugs by name and the chemical structures of the one or more drug pairs may be obtained from a database. Then at step 104, an analysis is performed on the chemical structures of the one or more pairs of drugs in a pair-wise manner (e.g., one drug pair at a time) to predict and identify potential DDI. Then at step 106, an analysis is performed to predict and identify one or more adverse events associated with the potential DDI identified at step 104. At step 108, the potential DDI from step 104 and potential adverse events from step 106 are sent as output to one or more devices. The devices used herein may be, for example, but not limited to, a smart watch, a portable device, a mobile phone, a tablet, a computer, etc.

FIG. 2 depicts a system 200 for implementing methodology 100 of FIG. 1. System 200 processing nodes 204-1 . . . 204-N, are configured to communicate over a network 220. Each of processing nodes 204-1 . . . 204-N may be configured as shown in computer system/server 204-1, which may include, but is not limited to, personal computer systems, server computer systems, thin clients, thick clients, hand-held or laptop devices, multiprocessor systems, microprocessor-based systems, programmable consumer electronics, network PCs, minicomputer systems, mainframe computer systems, and distributed cloud computing environments that include any of the above systems or devices, and the like. Computer system/server 204-1 may include one or more processors 206 coupled to a memory 210, a user interface 212 and a network interface 214. Processor 206 may comprise a DDI and adverse event prediction module 208 for implementing one or more steps of methodology 100 of FIG. 1. User interface 212 may be configured to enable user input into the computer system/server 204-1. Network interface 214 may be configured to enable the computer system/server 204-1 to interface with a network and other system components.

The computer system/server 204-1 may be configured to obtain and/or receive one or more drug pair inputs 202 (e.g., drug names or chemical structures) from one or more devices. Database 216 may store information relating to one or more drugs, the information may include the chemical structure of one or more drugs, DDIs and adverse events associated with one or more drug pairs, and/or store results from the analyses performed by DDI and adverse event prediction module 208. Data may periodically be transmitted between a user device for inputting one or more drug pairs and for receiving results of the DDI and adverse event prediction module 208, one or more databases 216 and the one or more processing nodes 204-1 . . . 204-N via network 220. Database 216 may be implemented within computing node 204-1 or apart from computing node 204-1. In certain embodiments, one or more of the databases 216 may be a publically available databases, such as the FDA Adverse Event Reporting System (FAERS). Network 220 may be a communication link comprising an interne connection, Ethernet link, local area link, cellular link, satellite link, global system for mobile communication (GSM), etc. It is to be appreciated that system 200 may include more or less components than shown in FIG. 2. For example, system 200 may include multiple ones of database 216, drug pair input 202 and may also include additional components suitable for implementing methodology 100 of FIG. 1.

FIG. 3 depicts an illustrative process for predicting and identifying DDI, according to an embodiment of the invention. The illustrative process shown in FIG. 3 delineates step 104 of FIG. 1. In this step, a prediction of DDIs is formulated via a bi-linear logistic regression and the probability of one or more DDIs of one or more drug pairs are generated as output for further processing to predict and identify one or more potential adverse events in the next step (delineated in the context of FIG. 4 below).

Initially, chemical structures 302 for one or more drug pairs and DDI labels 304 of the one or more drug-drug pairs may be received. The one or more drug pairs may be received from a user (e.g., a physician or patient) via a GUI on a device at the user end. In certain embodiments where the user enters drug names, the chemical structure corresponding to the drug name may be obtained from one or more sources (e.g., databases, websites, literature, etc.). One or more DDI labels 304 may be obtained from user input or from a database (e.g., FAERS or previously stored information in database 216).

Subsequently, the chemical structures 302 and labels of DDIs 304 can both be fed as input to a bi-linear regression model 306. The bi-linear logistic regression model 306 may then predict the probability of DDI 308 and optionally predict one or more chemical structures 310 that may contribute to DDI for each pair of drugs. For example, the prediction of the chemical structure for DDI 310 may be a specific fingerprint which would contribute to the DDI. As such, embodiments herein may identify incompatible chemical fingerprints for DDIs. It is to be noted that if DDI is not expected or predicted for a pair of drugs, then the methodology stops here and does not move on to predict DDI adverse events.

Figure 4:
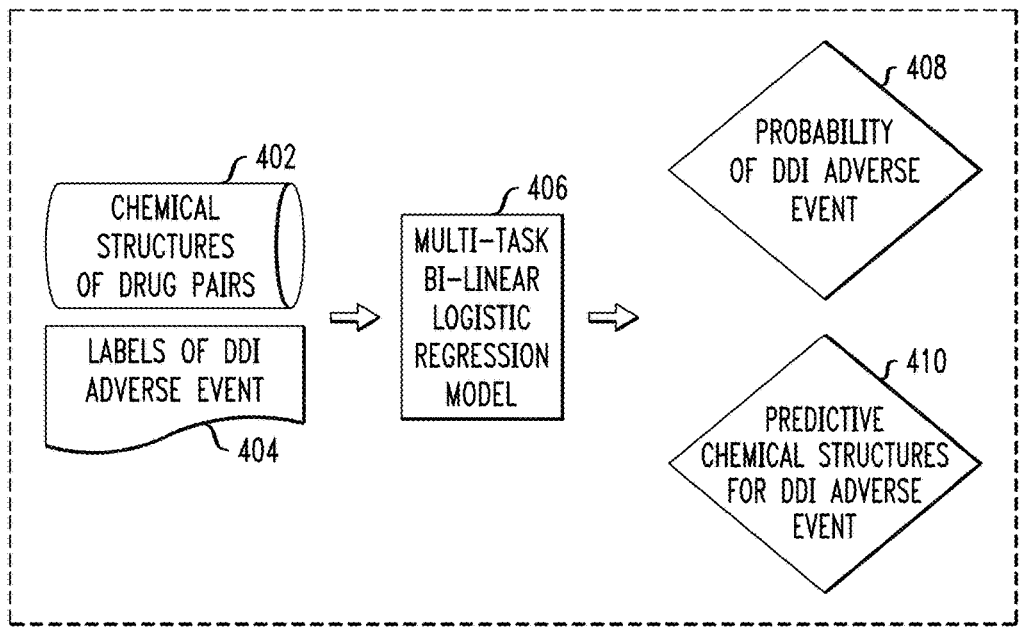
FIG. 4 illustrates an exemplary process for predicting DDI adverse events, according to an embodiment of the invention.

FIG. 4 depicts an illustrative process for predicting and identifying DDI adverse events, according to an embodiment of the invention. The illustrative process shown in FIG. 4 delineates step 106 of FIG. 1. In this step, the prediction of DDI adverse events is treated as a multi-label problem and multi-task bi-linear logistic regression is used to model the problem.

Initially, chemical structures 402 for one or more pairs of drugs and DDI adverse event labels 404 of the one or more drug pairs are obtained. Chemical structures 402 may be the same as chemical structures 302. DDI adverse event labels 404 may be represented as a "yes" or "no" (represented by "1" or "0") for each adverse event (e.g., bleeding, shortness of breath, nausea). The chemical structures 402 and DDI adverse event labels 404 may be obtained in a similar manner to chemical structures 302 and DDI labels 304.

Chemical structures 402 of the one or more drug pairs and labels of DDI adverse events 404 are both fed as input into a multi-task bi-linear logistic regression model 406. The multi-task bi-linear logistic regression model 406 may then predict the probability of DDI adverse event 408 and optionally identify predictive chemical structures 410 for DDI adverse events. Accordingly, embodiments herein may identify incompatible chemical fingerprints that lead to specific adverse events caused by DDIs.

Advantageously, the multi-task bi-linear logistic regression model 406 can take into account the possibility of multiple adverse events associated with each instance of DDI as well as possible associations between adverse events. As such, in this step, the system takes into consideration the possibility of multiple reasons for DDI. Each reason may be a "task," such that multiple reasons may be referred to as "multi-task" and a multi-task bi-linear regression model 406 may be used.

Accordingly, the output (step 108 in FIG. 1) of a system implementing an embodiment of the invention may include predicted probability of DDIs, predicted probability of the DDI adverse events, and predicted chemical structures that may contribute to DDI and DDI adverse events.

FIG. 5 shows an illustrative example of training a bi-linear model that may be used for DDI prediction as described above in step 104 of FIG. 1 and the bi-linear logistic regression model of FIG. 3. Initially, training data is received by the system implementing an embodiment of the invention. Training data may include chemical structure characteristics for various drugs and DDI labels of one or more drug-drug pairs. The chemical fingerprint of a drug can be obtained from the chemical structure of the drug. As used herein, a chemical fingerprint may refer to a unique pattern indicating the presence of particular molecules or chemical sub-structures of a chemical substance (e.g., a drug). Training data may be received from user input or from one or more databases (e.g., database 216). Based on the training data, whether or not a pair of drugs taken together would result in DDIs can be determined, and a label can be created for the pair of drugs. For example, the label may indicate whether or not a pair of drugs would result in DDI. The label may be represented by a "yes" or a "no" or it may be represented by binary numbers such as a "1" or a "0" for each pair of drugs.

Training a bi-linear model may further include training a data matrix, which includes information relating to the chemical fingerprint of a drug. As shown in matrix X, denoted as data matrix 501, each row may represent a drug and each column may represent a chemical sub-structure of the drug. For example, chemical structure 502 includes three benzene rings, a methyl group, two oxygen atoms, etc. In a row of data matrix 501 representing the drug corresponding to chemical structure 502, a column of the data matrix 501 representing benzene rings would contain a value of "3", a column of the data matrix 501 representing methyl groups would have a value of "1" and a column of the data matrix 501 representing oxygen atoms would contain a value of "2". The row in the matrix representing the drug with chemical structure 502 would also include values for other sub-structures of the drug. As such, each row in data matrix 501 defines the chemical fingerprint of a drug. Therefore, embodiments of the invention may receive a chemical structure as input and transfer the structure as a row in a data matrix (e.g., data matrix 501). Accordingly, the size of the matrix would grow as more drugs are included in the matrix.

Training a bi-linear model may also include training a label matrix. In matrix Y, denoted as label matrix 510, each cell (i,j) represents a DDI between drug i and drug j. Label matrix 510 may comprise the same number of rows and columns, the rows and columns representing the same set of drugs. If two drugs 512 are not compatible and would result in DDI, then the position in the matrix corresponding to the drug pair may be "1" else the position may be "0." For example, for i=1 and j=2, if these two drugs would interact and result in DDI, then the entry (1, 2) and entry (2, 1) will each have a label "1".

Bi-linear logistic regression may be performed on the chemical structure data for a drug pair and the labels associated with the drug pair. The bi-linear logistic regression may be computed as follows:

$$g(Y_{ij}) = x_i^T W x_j \qquad \text{Equation (1)}$$

The function $g(Y_{ij})$ graphically depicted in 522 is computed according to equation (1) above, where $Y_{ij}$ represents the label of DDI for a pair of drugs, such that if a pair of drugs results in DDI, then $Y_{ij}$ is one, otherwise it is zero. Once the coefficient matrix W 528 is learned from the data, the probability of DDI for a pair of drugs (e.g., drugs i and j) may be obtained via $g^{-1}(x_i^T W x_j)$. In equation (1) above, $x_i$ and $x_j$ are both d-dimensional column feature vectors and $W \in R^{d \times d}$ is the coefficient matrix. This method is considered "bi-linear" because the variables (i.e., $x_i$ and $x_j$) are independently linear, and the matrix 524 and matrix 526 are the same matrix X, with matrix 524 being the original X matrix and matrix 526 being matrix X transposed.

Figure 6:
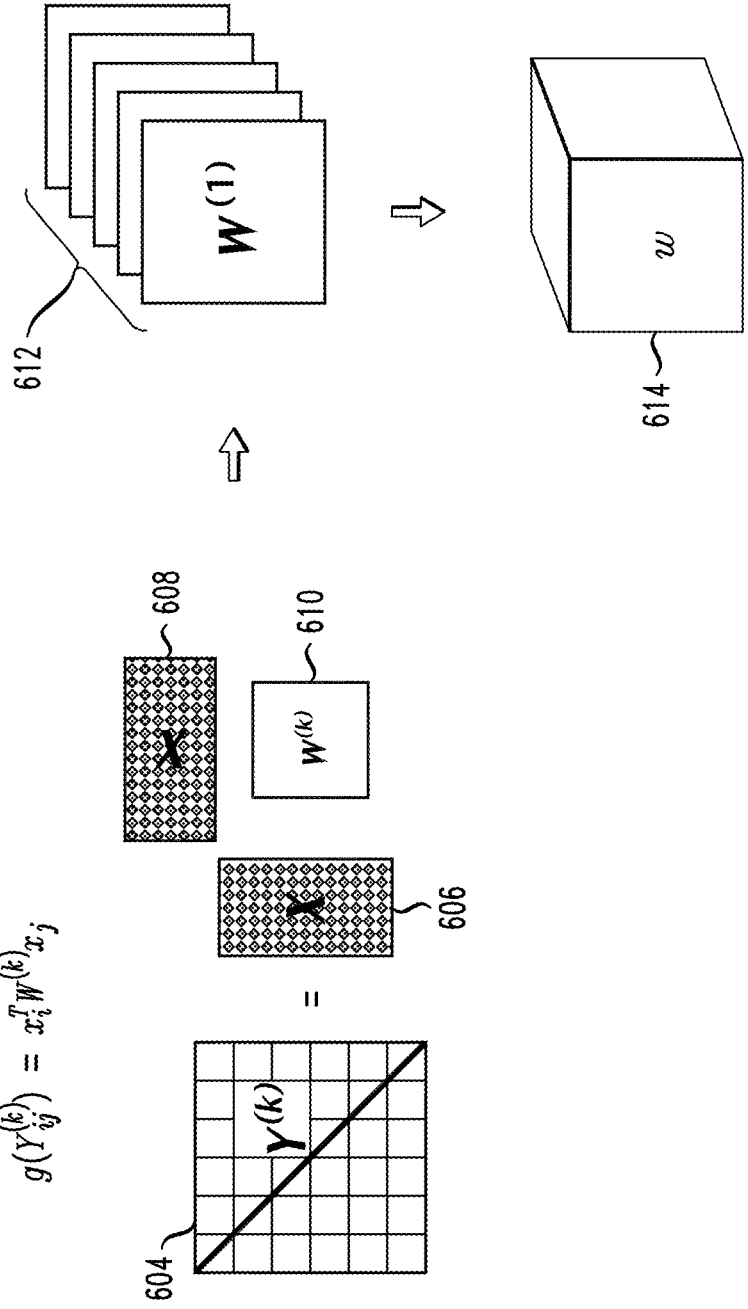
FIG. 6 illustrates a multi-task bi-linear model for predicting adverse events, according to an embodiment of the invention.

FIG. 6 shows an illustrative example of training a multi-task bi-linear model for DDI adverse events prediction as described above in step 106 and FIG. 4. Training data, as illustrated in data matrix 606 and 608, may include chemical structure characteristics for various pairs of drugs and DDI adverse event labels of one or more drug pairs. Chemical structure characteristics received may be the same as chemical structure characteristics received for training the bi-linear model for DDI prediction as described in FIG. 5. DDI adverse event labels may be represented as a "yes" or "no" (represented by "1" or "0") for each adverse event (e.g., bleeding, shortness of breath, nausea).

For example, given drug A and drug B, which is known to interact and cause dizziness, the DDI adverse event label for dizziness would be "1" for drug pair A and B. However, for drug A and drug C, which does not interact to cause dizziness, the DDI adverse event label for dizziness would be "0". If a pair of drugs (e.g., drugs A and B or drugs A and C) has multiple adverse events, each adverse event can be modeled as a "task" thereby resulting in a "multi-task" model. For example, drug pair A and B may also interact to cause other adverse events, such as, headache, swelling, irregular heartbeat, etc.

For each possible DDI adverse event (e.g., bleeding, dizziness, heart failure), a separate bi-linear model may be generated as follows:

$$g(Y_{ij}^{(k)}) = x_i^T W^{(k)} x_j \qquad \text{Equation (2)}$$

In equation (2) above, k denotes one possible adverse event, i.e., the index of the task. In equation (2) above, $x_i$, $x_j \in R^d$ are d-dimensional column feature vectors; $Y_{ij}^{(k)}$ is the label matrix (graphically depicted in 604) for the k-th adverse event where $Y_{ij}$ if the pair of drug i and drug j results in DDI for the k-th adverse event; $W^{(k)}$ 610 represents the model coefficient matrix for the k-th task (i.e., adverse event); and g(•) is the logit function. For example, if there are 1300 possible adverse events, 1300 different prediction models 612 (i.e., $W^{(k)}$, k=1, 2, . . . , 1300) can be trained using the methodology herein. The resulting models can then be combined as the W tensor 614, in other words, the 1300 coefficient matrices $W^{(k)}$, k=1, 2, . . . , 1300, are combined into one W tensor. A sparse group lasso can then be used to perform feature selection to select the significant features. The significant features are, for example, specific chemical fingerprints which may result in serious DDIs.

Illustratively, a user may input chemical structure of two drugs (e.g., carnitine and nicotine) into a system implementing an embodiment of the invention. Alternatively, the user may input two drug names, the system may then obtain the corresponding chemical structures for the drugs from one or more sources (e.g., a website or a database). Chemical fingerprints and DDI labels for each of the drugs may then be determined according to a process as described above in the context of FIGS. 3 and 5. The resulting feature vector and labels may then be fed to a bi-linear logistic regression model (trained according to an embodiment as described in FIG. 5) to determine the probability of DDI. If no DDI is expected for the drug pair, then the process stops at this point and an alert or message may be sent as output to the user and/or one or more devices to indicate that DDI is not likely to result between the given pair of drugs.

If the results of the bi-linear regression model indicates a probability of DDI, the system then proceeds to predict potential DDI adverse events for the given drug pair (e.g., hypoventilation, insomnia, neuropathy). At this step, a multi-task bi-linear logistic regression model, such as that described in FIGS. 4 and 6, may be used. The resulting predicted DDI adverse events may then be sent as output to the user and/or one or more devices in the form of an alert and/or message.

Advantageously, various embodiments of the invention provide benefits in predicting DDI between one or more pairs of drugs and predicting potential adverse events associated with the DDIs. For example, various embodiments herein may inform a user if certain drugs can be taken together and what types of adverse events can occur if the drugs are taken together.

Embodiments of the present invention may be a system, a method, and/or a computer program product at any possible technical detail level of integration. The computer program product may include a computer readable storage medium (or media) having computer readable program instructions thereon for causing a processor to carry out aspects of the present invention. For example, computer system/server 204-1 may comprise a computer program product for implementing embodiments of the invention disclosed herein.

The computer readable storage medium (e.g., memory 210) can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network (e.g., network 220), including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is understood in advance that although this disclosure includes a detailed description on cloud computing below, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 7:
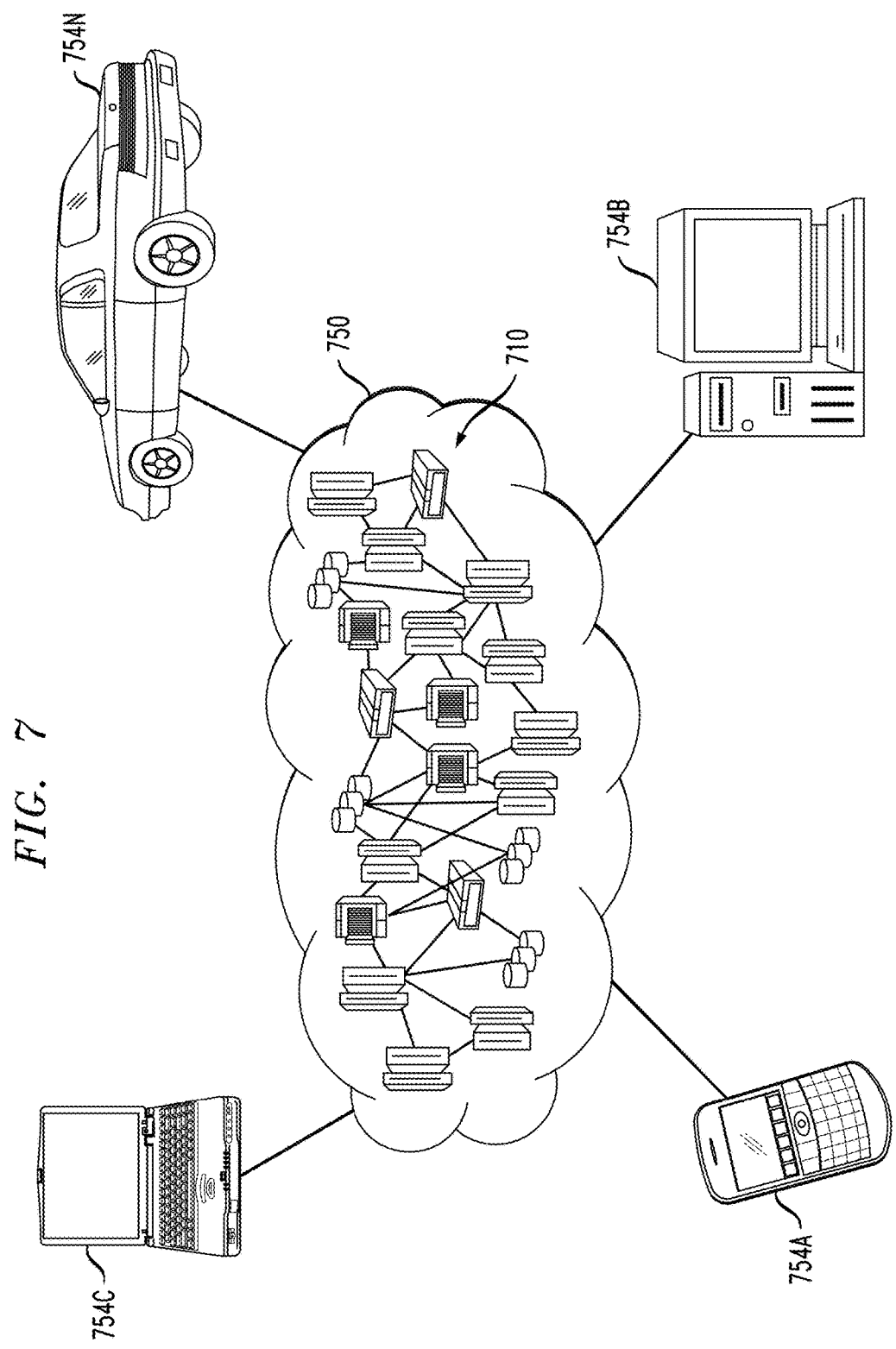
FIG. 7 illustrates a cloud computing environment according to an embodiment of the invention.

Referring now to FIG. 7, illustrative cloud computing environment 750 is depicted. As shown, cloud computing environment 750 comprises one or more cloud computing nodes 710 with which local computing devices used by cloud consumers, such as, for example, a wearable device (not explicitly shown), a personal digital assistant (PDA) or cellular telephone 754A, desktop computer 754B, laptop computer 754C, and/or automobile computer system 754N may communicate. Nodes 710 may communicate with one another. They may be grouped (not shown) physically or virtually, in one or more networks, such as Private, Community, Public, or Hybrid clouds as described hereinabove, or a combination thereof. This allows cloud computing environment 750 to offer infrastructure, platforms and/or software as services for which a cloud consumer does not need to maintain resources on a local computing device. It is understood that the types of computing devices 754A-N shown in FIG. 7 are intended to be illustrative only and that computing nodes 710 and cloud computing environment 750 can communicate with any type of computerized device over any type of network and/or network addressable connection (e.g., using a web browser).

Figure 8:
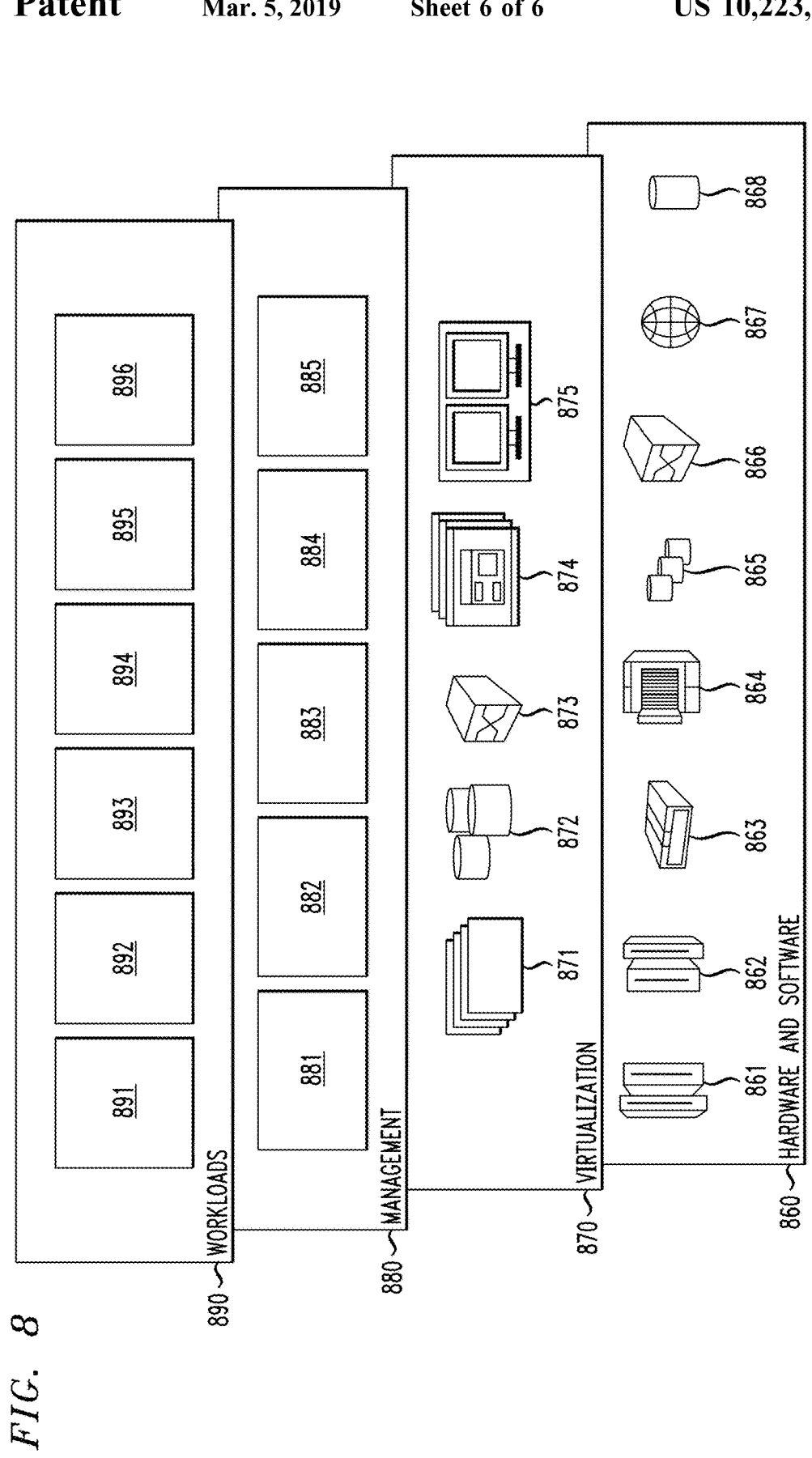
FIG. 8 depicts abstraction model layers according to an embodiment of the invention.

Referring now to FIG. 8, a set of functional abstraction layers provided by cloud computing environment 750 (FIG. 7) is shown. It should be understood in advance that the components, layers, and functions shown in FIG. 8 are intended to be illustrative only and embodiments of the invention are not limited thereto. As depicted, the following layers and corresponding functions are provided:

Hardware and software layer 860 includes hardware and software components. Examples of hardware components include: mainframes 861; RISC (Reduced Instruction Set Computer) architecture based servers 862; servers 863; blade servers 864; storage devices 865; and networks and networking components 866. In some embodiments, software components include network application server software 867 and database software 868.

Virtualization layer 870 provides an abstraction layer from which the following examples of virtual entities may be provided: virtual servers 871; virtual storage 872; virtual networks 873, including virtual private networks; virtual applications and operating systems 874; and virtual clients 875.

In one example, management layer 880 may provide the functions described below. Resource provisioning 881 provides dynamic procurement of computing resources and other resources that are utilized to perform tasks within the cloud computing environment. Metering and Pricing 882 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 883 provides access to the cloud computing environment for consumers and system administrators. Service level management 884 provides cloud computing resource allocation and management such that required service levels are met. Service Level Agreement (SLA) planning and fulfillment 885 provide pre-arrangement for, and procurement of, cloud computing resources for which a future requirement is anticipated in accordance with an SLA.

Workloads layer 890 provides examples of functionality for which the cloud computing environment may be utilized. Examples of workloads and functions which may be provided from this layer include: mapping and navigation 891; software development and lifecycle management 892; virtual classroom education delivery 893; data analytics processing 894; transaction processing 895; and DDI and adverse event prediction 896, which may perform one or more of the functions described above.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for drug-drug interaction and adverse event analysis, the method comprising:
    obtaining chemical structures for one or more pairs of drugs from at least one of a user and a database;
    generating a chemical fingerprint for each drug of the one or more pairs of drugs, wherein the chemical fingerprint for each drug comprises a unique pattern indicating a presence of particular molecules or chemical sub-structures obtained from the chemical structure of the drug;
    performing a drug-drug interaction prediction for each pair of drugs comprising inputting the chemical fingerprint of each drug of a pair of drugs and a drug-drug interaction label for the pair of drugs into a bi-linear logistic regression model to generate a probability of a drug-drug interaction between the pair of drugs;
    in response to receiving that the probability of the drug-drug interaction between the pair of drugs is expected or predicted, performing an adverse event prediction based on the predicted drug-drug interaction for the one or more pairs of drugs; and
    transmitting results of at least one of the drug-drug interaction prediction and the adverse event prediction to one or more devices, wherein the results increase the usage safety of the one or more pairs of drugs;
    wherein the steps are performed by at least one processor device coupled to a memory.

2. The method of claim 1, wherein the bi-linear logistic regression model further generates one or more chemical structures contributing to drug-drug interaction of the pair of drugs.

3. The method of claim 1, wherein performing adverse event prediction comprises utilizing a multi-task bi-linear logistic regression model.

4. The method of claim 1, wherein the chemical fingerprint of each drug of a pair of drugs and one or more adverse event labels for the pair of drugs are inputted to the multi-task bi-linear logistic regression model to generate a probability for each of the one or more adverse event labels for the pair of drugs.

5. The method of claim 1, further comprising training a drug-drug interaction model for predicting drug-drug interactions.

6. The method of claim 5, wherein training the drug-drug interaction model comprises training a data matrix comprising chemical fingerprints for one or more drugs.

7. The method of claim 6, wherein each row of the data matrix represents the chemical fingerprint of a drug.

8. The method of claim 7, wherein each column of the data matrix represents a chemical sub-structure of the drug.

9. The method of claim 5, wherein training the drug-drug interaction model further comprises training a label matrix comprising drug-drug interaction labels for one or more drug pairs.

10. The method of claim 9, wherein each drug-drug interaction label comprises information representing whether a pair of drugs would result in drug-drug interaction.

11. The method of claim 1, further comprising training an adverse event model for predicting one or more adverse events for one or more pairs of drugs.

12. The method of claim 11, wherein training the adverse event model comprises training a separate model for each adverse event.

13. The method of claim 12, further comprising combining the separate models into a tensor.

14. The method of claim 13, further comprising applying a sparse group Lasso algorithm to the tensor.

15. The method of claim 1, wherein the chemical fingerprint comprises chemical sub-structures of the drug.

16. An apparatus for drug-drug interaction and adverse event analysis, the apparatus comprising:
   a memory and a processor operatively coupled to the memory to implement a method comprising:
      obtaining chemical structures for one or more pairs of drugs from at least one of a user and a database;
      generating a chemical fingerprint for each drug of the one or more pairs of drugs, wherein the chemical fingerprint for each drug comprises a unique pattern indicating a presence of particular molecules or chemical sub-structures obtained from the chemical structure of the drug;
      performing a drug-drug interaction prediction for each pair of drugs comprising inputting the chemical fingerprint of each drug of a pair of drugs and a drug-drug interaction label for the pair of drugs into a bi-linear logistic regression model to generate a probability of a drug-drug interaction between the pair of drugs;
      in response to receiving that the probability of the drug-drug interaction between the pair of drugs is expected or predicted, performing an adverse event prediction based on the predicted drug-drug interaction for the one or more pairs of drugs; and
      transmitting results of at least one of the drug-drug interaction prediction and the adverse event prediction to one or more devices, wherein the results increase the usage safety of the one or more pairs of drugs.

17. A computer program product for drug-drug interaction and adverse event analysis, the computer program product comprising a computer readable storage medium for storing computer readable program code which, when executed, causes a computer to:
   obtain chemical structures for one or more pairs of drugs from at least one of a user and a database;
   generate a chemical fingerprint for each drug of the one or more pairs of drugs, wherein the chemical fingerprint for each drug comprises a unique pattern indicating a presence of particular molecules or chemical sub-structures obtained from the chemical structure of the drug;
   perform a drug-drug interaction prediction for each pair of drugs comprising inputting the chemical fingerprint of each drug of a pair of drugs and a drug-drug interaction label for the pair of drugs into a bi-linear logistic regression model to generate a probability of a drug-drug interaction between the pair of drugs;
   in response to receiving that the probability of the drug-drug interaction between the pair of drugs is expected or predicted, perform an adverse event prediction based on the predicted drug-drug interaction for the one or more pairs of drugs; and
   transmit results of at least one of the drug-drug interaction prediction and the adverse event prediction to one or more devices, wherein the results increase the usage safety of the one or more pairs of drugs.

* * * * *